United States Patent [19]

Keromnes et al.

[11] Patent Number: 5,017,003
[45] Date of Patent: May 21, 1991

[54] AUTOMATIC SORTING OVOSCOPE

[75] Inventors: Bernard Keromnes, Morlaix; Jean-Pierre Breuil, Taule, both of France

[73] Assignee: Breuil, S.A., Landivisiau, France

[21] Appl. No.: 415,329

[22] PCT Filed: Jan. 19, 1989

[86] PCT No.: PCT/FR89/00015
§ 371 Date: Sep. 20, 1989
§ 102(e) Date: Sep. 20, 1989

[87] PCT Pub. No.: WO89/06797
PCT Pub. Date: Jul. 27, 1989

[30] Foreign Application Priority Data

Jan. 20, 1988 [FR] France ................................ 88 00628

[51] Int. Cl.$^5$ ............................................. G01N 33/08
[52] U.S. Cl. ...................................... 356/53; 209/510
[58] Field of Search ..................... 356/52, 53, 60, 66, 356/69, 57; 209/510, 511, 643

[56] References Cited

U.S. PATENT DOCUMENTS 1,987,336  1/1935  Powell ..................................... 356/57
4,805,778  2/1989  Nambu .................................... 209/243

FOREIGN PATENT DOCUMENTS 1287741  10/1969  Fed. Rep. of Germany .
2455282  11/1980  France .
968962  9/1964  United Kingdom .

Primary Examiner—Vincent P. McGraw
Assistant Examiner—LaCharles P. Keesee
Attorney, Agent, or Firm—Sandler, Greenblum & Bernstein

[57] ABSTRACT

The automatic sorter ovoscope of the invention is characterized in that it comprises a light box (6) arranged under a candling head (1) which is provided with at least one suction cup (9) intended to take by suction eggs, one by one, and which is provided with vacuum means and with light sensitive means, while a device for controlling the vacuum means allows to apply by suction each suction cup to an egg to be candled and to appreciate its transparency as a function of the light intensity coming from the light box (6) and reaching the light sensitive means, the control device being servo-controlled by the signal from said light sensitive means so that the suction cup may retain by suction the egg when the signal from the light sensitive means indicates that a predetermined transparency of the egg is exceeded.

17 Claims, 3 Drawing Sheets

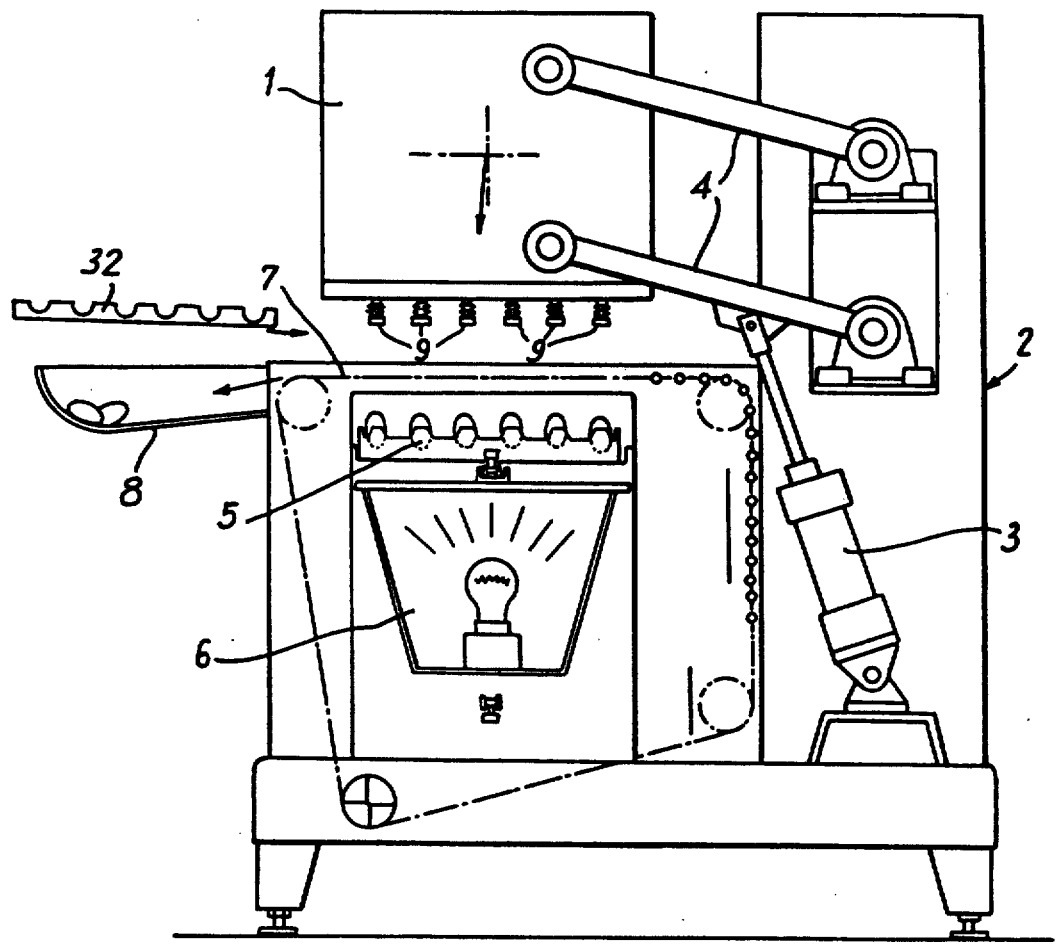

AUTOMATIC SORTING OVOSCOPE

BACKGROUND OF THE INVENTION

1. Field of the Invention

The invention relates to an automatic sorting candler.

Eggs are candled to observe their interiors so as to ascertain the the state of their contents.

This candling operation has the particular purpose of verifying the incubation state or to look for various possible changes in the eggs.

2. Description of the Prior Art

It is particularly common to candle of eggs near the 18th day of incubation so as to be able to transfer to hatching baskets the "good eggs" and eliminate the clear eggs, i.e. eggs which are not fertilized. It is also possible to proceed to this candling operation with a view towards to removing the rotten eggs, the eggs invaded by mildew, putrefied eggs, containing dead embryos, etc. Up until the present, candling was done directly by hand or by means of a candling lamp or candler. The conventional candler is equipped with a light source to make it possible to appraise in the egg the transparency state of the eggs. However, one has sought to design more sophisticated equipment capable of measuring the transparency state of eggs.

A problem with automating this type of operation rests in the sorting after candling between the good eggs and the defective eggs.

SUMMARY OF THE INVENTION

The invention proposes an automatic sorting candler, which is remarkable in that it comprises a light box provided underneath a candling head which is furnished with at least one suction cup adapted to take hold of eggs individually by suctioning and which is equipped with a vacuum means and a light sensitive means, while a control device for the vacuum means makes it possible to apply by suctioning each suction cup onto an egg to be candled and to appraise the transparency as a function of the output of the light coming from the light box and reaching the sensitive means, while the control device is servo-controlled by the signal of said light sensitive means, such that said suction cup can retain by suctioning the egg when the signal of the light sensitive means indicates that a certain predetermined transparency of said egg has been exceeded.

Preferably, the candling head is mounted in a vertically movable manner above a routing conveyor and an evacuation conveyor, all to evacuate, after candling, the defective eggs by means of the evacuation conveyor, to recover, after candling, the good eggs by means of the routing conveyor and to bring a new batch of eggs to be candled by means of said routing conveyor.

According to an embodiment, the automatic sorting candler further comprises a transfer conveyor adapted to receive, after candling, the good eggs, which are transferred by means of the candling head, from the routing conveyor, to said transfer conveyor.

Preferably, the vacuum means of each suction cup comprises a suctioning conduit of which one of the ends opens into the bottom of said suction cup and of which the other end is connected to a vacuum pump by means of an electrovalve, while the light sensitive means is an infrared phototransistor, and the light box is provided with means to produce the infrared light.

To control the good operation of the apparatus, it can comprise a control system which makes it possible to control the correct detection of absence of light be each sensitive means when the light box is switched off and the suction cup in question is applied under a vacuum to an egg. In this case, it is preferably provided with a means for display of poor operation of the controlled suction cup, as well as a means which makes it possible to isolate said suction cup in case of detected breakdown.

According to another embodiment, the automatic sorting candler is further comprised of a suction cup, a comparator provided to compare the signal of the corresponding light sensitive means with at least one predetermined signal, generated by a generator of threshold signals, so as to create a detection signal which is a function of the comparison of said signals. Then, the threshold signal generator is provided to generate at least one predetermined signal of comparison which corresponds to a selected threshold of transparency, so as to be able to create a detection signal which is a function of exceeding or not exceeding this threshold. Preferably, the threshold signal generator is provided to generate in addition a predetermined signal of comparison which corresponds to a threshold of light absence, so as to be able to create a detection signal, called "black test", which is a function of exceeding or not exceeding this threshold.

In the case of an embodiment of the previously cited type, the detection signal, after storing, can be used to act on the control of the vacuum means, so as to maintain the vacuum of the corresponding suction cup when said signal indicates a selected threshold has been exceeded.

Preferably, the candler comprises a control robot, which makes it possible to control the selection of the predetermined comparison signal, to control the storing of the detection signal and to control a possible stop of the apparatus when the black test signal connected in return to said robot, is bad.

In addition, it can be important to know the proportions between the good eggs and the defective eggs according to the loads. An apparatus according to the invention correctly makes it possible to easily establish these ratios. The apparatus is comprised of a means for measuring the electric current used by at least one part of the apparatus and a calculator provided so as to determine with respect to the information of said measuring apparatus, numerical ratios between the number of defective eggs and the number of good eggs.

BRIEF DESCRIPTION OF THE DRAWINGS

The invention will be better understood and other characteristics will appear upon reading the description which follows and which refers to the annexed drawings in which:

FIG. 1 shows in elevation an apparatus according to the invention,

DESCRIPTION OF THE PREFERRED EMBODIMENTS

Figure 3:
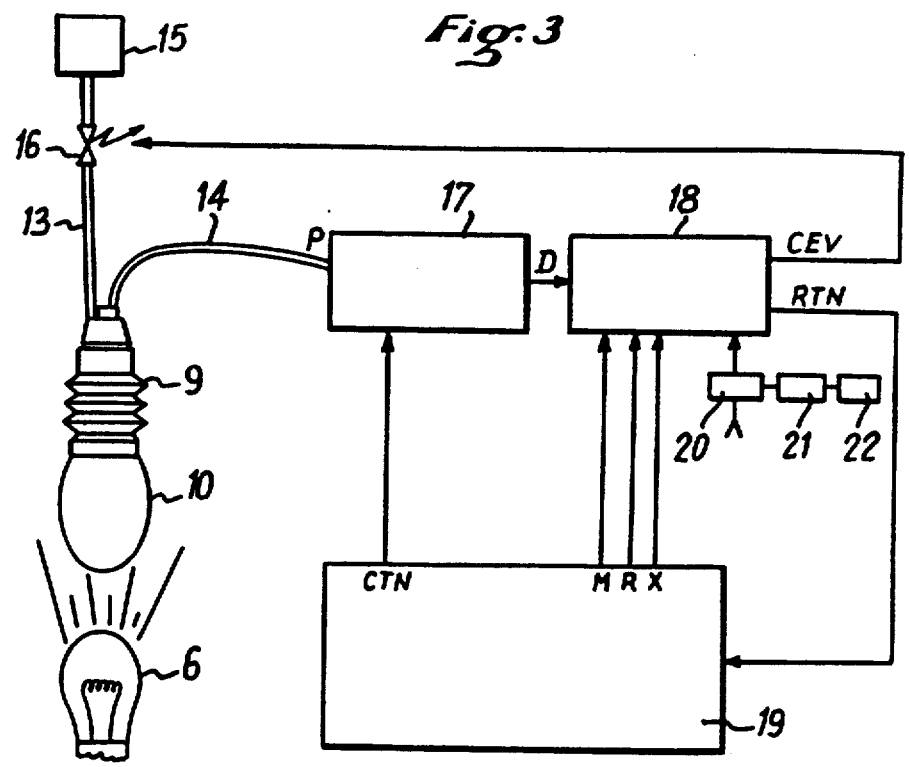
FIG. 3 is a general control diagram of the apparatus.

FIG. 1 shows a head 1, called candling, which is mounted in a vertically movable manner on a frame 2 by means of at least one jack 3 and hinged arms such as 4.

The head 1 is actuated by a vertical movement above a routing conveyor 5, in the form, for example, of a succession of egg baskets, while said conveyor is moved over a light box 6, provided to produce an infrared light for the reasons called forth below.

FIG. 1 also shows an evacuation conveyor 7, in the form of a belt with bars, which passes near a receiver 8 for recovery. The head 1 comprises a plurality of suction cups, such as 9, whose number corresponds to that of the egg housings of each basket of conveyor 5, said baskets being further punched underneath to allow the light to go through.

Figure 2:
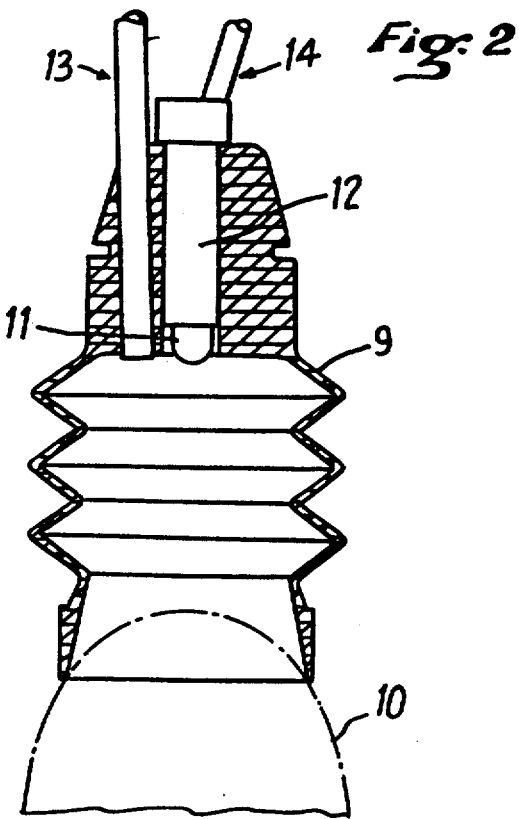
FIG. 2 shows in detail one of the suction cups for measuring and gripping.

A suction cup 9 is seen in more in detail in FIG. 2. It is appropriate to consider the term suction cup in its broadest sense. It can involve a sort of vacuum bell jar of appropriate material. Its role is to be able to apply itself in a sealed manner to an egg to be tested, such as 10. This sealed application has a double aim; it involves, on the one hand, avoiding parasitic light entries at the time of the candling and, on the other hand, ensuring the possibility of gripping by suctioning, as will be explained below. Each suction cup, of flexible rubber, for example, is provided, in its upper part, with an infrared phototransistor 11, embedded in a polyester resin 12, and with a suctioning conduit 13. The phototransistor is connected to an ironclad cable 14.

FIG. 3 shows schematically the device of FIG. 2 connected to various elements.

The suctioning conduit 13 is connected to a vacuum pump 15, by means of an electrovalve 16, while the cable 14 is connected to an electronic card 17, itself connected to another card 18. The cards 17 and 18 are controlled by a control robot 19, adapted to generate several signals CTN, M, R and X, respectively. In addition, the card 18 receives an electrical supply by means of a current measurer 20, connected to an analog to digital converter 21 and a calculator 22 whose functions will be specified below.

Figure 4:
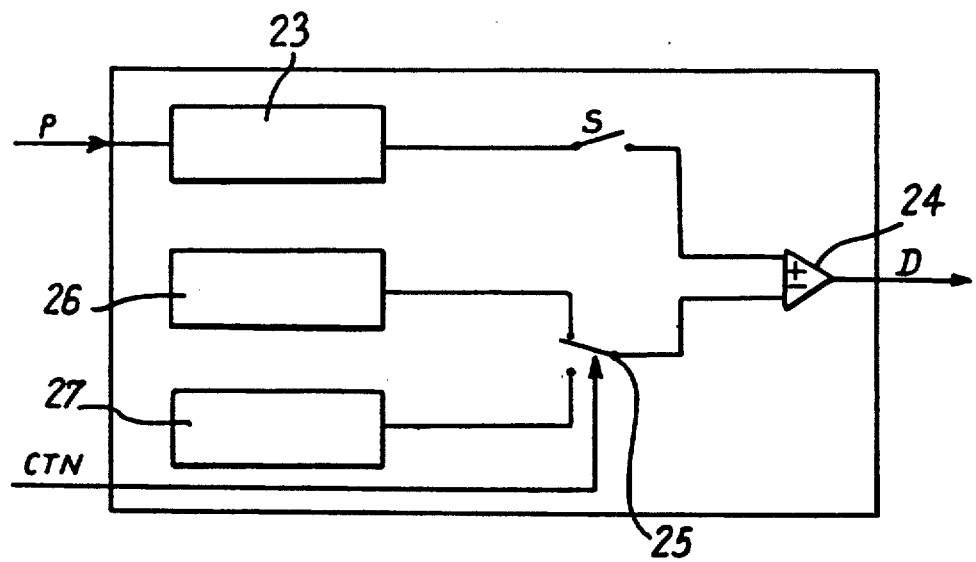
FIGS. 4 and 5 show more in detail the electronic cards of FIG. 3.

The cable 14 connected to the phototransistor, directs a signal P to the input of card 17, as FIGS. 3 and 4 show. This signal P is amplified in an amplification stage 23, which is connected by means of a circuit breaker S at one of the inputs of a comparator 24. The other input of the comparator 24 is connected to a reversing switch 25 which is provided to connect to the selection a threshold apparatus 26 or 27 and which is controlled by the CTN signal coming from the robot 19.

The comparator 24 delivers a detection signal D which is sent into a memory 28 (FIG. 5) controlled by the signal M of storage, coming from the robot 19 (FIG. 2), the memory 28 being also capable of receiving the signal R for memory dump coming from the robot 19.

The outlet of the memory 28 is connected to a display diode 29 and to one of the inputs of an electronic door 30, of the "OU" type, whose other input receives the signal X coming from the robot 19 (FIG. 3). The output signal of the memory 28 is likewise looped in return on the robot 19 (signal RTN of FIGS. 3 and 5).

The output of the door 30 is connected to a relay 31 which delivers a signal CEV which, as FIG. 3 shows, is adapted to control the electrovalve 16.

The operation of the apparatus is simple to understand and there will be described below an operation cycle.

The apparatus is in the initial position, as shown in FIG. 1, i.e. the candling head 1 is raised. The conveyor 5 brings a plate of eggs to be tested under the head 1 which begins its descent on the eggs, such that each suction cup 9 is applied to an egg 10, as FIG. 2 shows.

So as to ensure a perfect sealing of each suction cup, the robot 19 makes it possible to send the signal X, which stimulates the relay 30 to generate the control signal CEV, so as to activate electrovalve 16 and to make it possible, by means of conduit 13 and pump 15, to create a partial vacuum in said suction cup. At the same time, the signal X or another distinct signal (CTN signal for example), makes it possible to switch off the light box 6. In these circumstances, the phototransistor 11 of each suction cup should not in principle deliver any signal or only extremely weak signals P, even after the amplification stage 23. This process makes it possible in fact to test the good condition of each suction cup. This test, called "black test" is carried out by means of the CTN command of the robot 19 ("black test" command) which acts on the reversing switch 25 (FIG. 4) to connect the apparatus 27 to the input of comparator 24. The apparatus 27 is provided to generate a signal which corresponds substantially to an absence of light reception, i.e. to a predetermined threshold of control (black test threshold).

In this case, if the suction cup is correct, the detection signal D, coming from the comparison between the signal P and the control threshold signal, and which arrives at the memory 28, is practically nil.

On the other hand, the slightest defect leads to exceeding the control threshold, which activates the diode 29, thus displaying the defective suction cup, while the signal RTN for return makes it possible, upon returning to the robot 19 for example, to stop the machine.

It is also significant to note that the circuit breaker S makes it possible to isolate (by opening it as shown in FIG. 4), the defective suction cup so as to be able to continue the operation cycle.

After this periodical or systematic control, one acts again on the reversing switch 25 to connect the apparatus 26 (as shown in FIG. 4), which is provided to create a predetermined threshold signal called candling. This threshold depends on the state of transparency that one wishes to detect. The light box 6 is then lighted, the infrared used making it possible to avoid the exterior incidences and to proceed easily into a place which is lighted naturally or artificially.

The comparator 24 then generates a signal D, either very weak, or nil, if the signal P, after amplification, exceeds the candling threshold signal. The signal M for storage makes it possible to store the signal D in memory 28. In case of exceeding the threshold (egg considered too transparent), the diode 29 lights up (displaying the suction cup which detects a defective egg, and, especially, the relay 31 remains stimulated by means of the door 30, even if the control signal X is cancelled.

After setting the signal X at zero, the head 1 is raised and it is clear that only the defective eggs remain held by suctioning (active CEV command).

Figure 5:
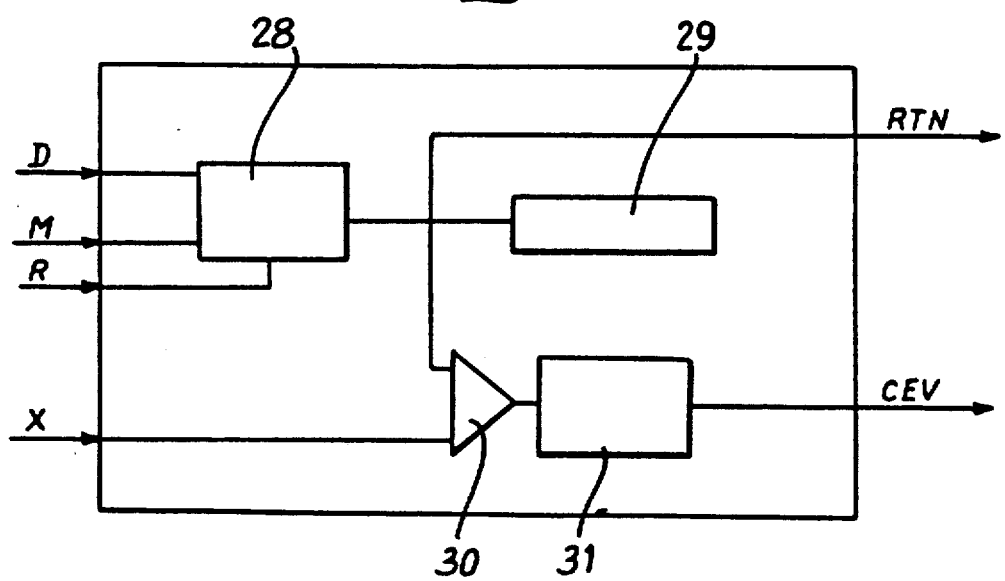

It then suffices to advance the conveyor 7, in the form of a belt with bars, under the head 1, and to release the raised eggs by eliminating the vacuum maintained in the suction cups. To cancel the suction, it suffices to cut off the electrical supply of electrovalves 16, by possible means of relays 31. To eliminate suction, it is still possible to simply dump the memory 28 by means of the signal R that resets to zero (FIG. 3 and 5).

After this operation, the conveyor 7 advances, as FIG. 1 shows and dumps the defective eggs into the recovery tank 8.

It is then possible to bring a new plate of eggs by advancing the conveyor 5 and to recover the good eggs.

It is also possible to transfer the good eggs from conveyor 5 to another transfer conveyor, schematized in 32 in FIG. 1. The passage from conveyor 5 to conveyor 32 is obviously done with head 1, which takes the eggs by suctioning from conveyor 5 to bring them to said conveyor 32 (the means for this movement being provided on head 1), unless there is provided, as FIG. 1 shows, a possible lateral displacement of conveyor 32, which is placed under the head 1 to receive the good eggs.

As FIG. 3 shows, the electrical supply of the electrovalves can be measured by a measuring device 20 (measurement of intensity and/or voltage and/or consumption), which is connected to the analog to digital converter 21 which delivers a signal to the calculator 22.

Thus, it is possible, by measuring the electric current used by the electrovalves at the moment when the head is raised with the defective eggs, to calculate by the calculator 22, the number of said defective eggs. This type of calculation which makes it possible to particularly establish ratios between the good eggs and the defective eggs, can of course be done in any other manner, from the moment when the apparatus is capable of separating and displaying the eggs depending on their nature. The measurement of the current used can be taken on another part of the apparatus, just as it is possible to directly send into the calculator, signals in the form of impulses created from detection signals D at the moment of candling (i.e. the comparison between said signals D and signals of candling threshold).

Numerous modifications or alternatives can obviously be brought about without going beyond the scope of the invention. Apart from the number of suction cups 9, the number of conveyors and movements between them which can differ with respect to the description which precedes, other characteristics can be conceived. This is why, for example, light of the infrared type is not absolutely necessary, the vacuum means can be realized in the form of simple valves, that the apparata 26 and 27 can be more numerous and/or adjustable so as to establish several possible test thresholds for example.

The apparata 26 and 27 and the reversing switch 25 can also be replaced by a single generator capable of delivering several signals according to preference.

We claim:

1. An automatic sorting candler, comprising:
   (a) a light box;
   (b) a candling head above said light box, said candling head comprising at least one suction cup to hold an egg by suction, each said at least one suction cup including means for holding an egg by vacuum, and light sensitive means for detecting transmitted light and providing a signal; and
   (c) control means for evaluating the transparency of eggs with respect to output of light emanating from said light box, said control means being associated with said light sensitive means and said means for holding an egg by vacuum to permit each said at least one suction cup to hold an egg by suction when the signal of the light sensitive means indicates that a predetermined transparency of the egg has been exceeded.

2. The automatic sorting candler according to claim 1, further comprising an evacuation conveyor for removing defective eggs after detection by said control means.

3. The automatic sorting candler according to claim 2, further comprising a routing conveyor for routing eggs held by suction after the signal is transmitted by said light sensitive means, and for transporting a new batch of eggs to be candled.

4. The automatic sorting candler according to claim 3, wherein said candling head is mounted for vertical movement above said routing conveyor and said evacuation conveyor.

5. The automatic sorting candler according to claim 3, further comprising a transfer conveyor for receiving eggs from said routing conveyor.

6. The automatic sorting candler according to claim 1, wherein said means for holding an egg by vacuum includes a suction conduit having one end opening of a respective suction cup and another end connected to a vacuum pump.

7. The automatic sorting candler according to claim 6, further including an electrovalve in the said suction conduit.

8. The automatic sorting candler according to claim 1, wherein said light sensitive means includes an infrared phototransistor.

9. The automatic sorting candler according to claim 1, wherein the light box includes a means for emitting infrared light.

10. The automatic sorting candler according to claim 1, wherein said control means includes means for testing each said at least one suction cup to detect presence of light when said light box is switched off and the suction cup is holding an egg by vacuum.

11. The automatic sorting candler according to claim 10, wherein said means for testing include means for display and isolation of a malfunctioning suction cup.

12. The automatic sorting candler according to claim 1, wherein said control means include a comparator and a threshold signal generator, said comparator being capable of comparing the signal of a corresponding light sensitive means with at least one predetermined signal generated by the threshold signal generator, with said comparator being capable of creating a detection signal which is a function of the comparison of the signals.

13. The automatic sorting candler according to claim 12, wherein said at least one predetermined signal corresponds to a selected transparency threshold, and the detection signal is a function of whether said selected transparency threshold is exceeded.

14. The automatic sorting candler according to claim 12, wherein said threshold signal generator is capable of generating a predetermined signal for comparison corresponding to an absence of light threshold, and a black test detection signal is capable of being created which is a function of whether said absence of light threshold is exceeded.

15. The automatic sorting candler according to claim 12, wherein said control means further include means for storing said detection signal, and means for transmitting the stored detection signal to means for maintaining the vacuum of a corresponding suction cup when the detection signal indicates that a preselected threshold has been exceeded.

16. The automatic sorting candler according to claim 14, wherein said control means further include a control robot for controlling selection of said predetermined comparison signal, storage of said detection signal and stopage of operation when said absence of light threshold detects a defective suction cup.

17. The automatic sorting candler according to claim 12, further comprising a calculator and means for measuring electrical current used by at least one part of said control means to determine numerical ratios between the number of eggs held by the suction cups and the number of eggs released by the suction cups.

* * * * *

UNITED STATES PATENT AND TRADEMARK OFFICE
CERTIFICATE OF CORRECTION

PATENT NO. : 5,017,003

DATED : May 21, 1991

INVENTOR(S) : Keromnes et al

It is certified that error appears in the above-identified patent and that said Letters Patent is hereby corrected as shown below:

Column 1, line 13, "of" should be deleted.
Column 1, line 18, "to" should be deleted.
Column 1, line 8, "the" (second occurrence) should be deleted.
Column 2, line 3, "be" should be changed to --by--.
Column 6, line 32, (claim 10, line 2) "includes" should be changed to --include--.

Signed and Sealed this

Twenty-second Day of November, 1994

BRUCE LEHMAN

*Attest:*

*Attesting Officer*

*Commissioner of Patents and Trademarks*